United States Patent [19]

Mueller et al.

[11] 4,130,021

[45] Dec. 19, 1978

[54] ULTRASONIC SECTOR SCANNING SEARCH UNIT

[75] Inventors: Peter G. Mueller, Guilford; Albert S. Goodrich, Newtown, both of Conn.

[73] Assignee: Picker Corporation, Cleveland, Ohio

[21] Appl. No.: 741,413

[22] Filed: Nov. 12, 1976

[51] Int. Cl.$^2$ .................................... G01N 29/00
[52] U.S. Cl. ............................................ 73/633
[58] Field of Search ............ 73/67.8 S, 71.5 US, 73/67.8 R, 67.7, 67.5 R, 618, 633, 635, 639; 128/2 V, 2.05 Z

[56] References Cited

U.S. PATENT DOCUMENTS

| 3,257,843 | 6/1966 | Cowan | 73/67.8 S |
| 3,308,652 | 3/1967 | Appel et al. | 73/67.8 S |
| 3,369,415 | 2/1968 | Slawsky | 73/67.8 S |
| 3,547,101 | 12/1970 | Rosauer | 128/2 V |
| 3,752,255 | 8/1973 | Hill et al. | 73/67.8 S |
| 3,996,792 | 12/1976 | Kubota et al. | 73/67.8 S |

*Primary Examiner*—Stephen A. Kreitman

[57] ABSTRACT

A sector scanning search unit which supports a transducer for oscillation about a virtual pivot axis extending medially across the face of the transducer. The scanner unit is an elongate hand held unit in which the transducer is supported near one end of a chassis. The transducer's face is oriented transversely of a longitudinal axis of the chassis and on a side of the transducer opposite its supporting structure. The sector scanner is also provided with a mechanism for readily adjusting the magnitude of the sector being scanned, even while such scanning is taking place.

6 Claims, 7 Drawing Figures

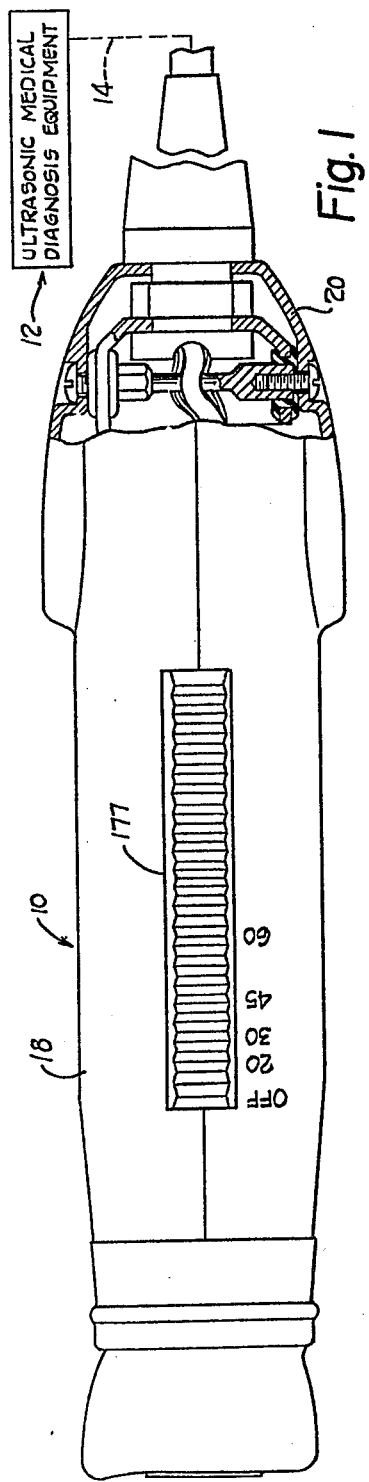

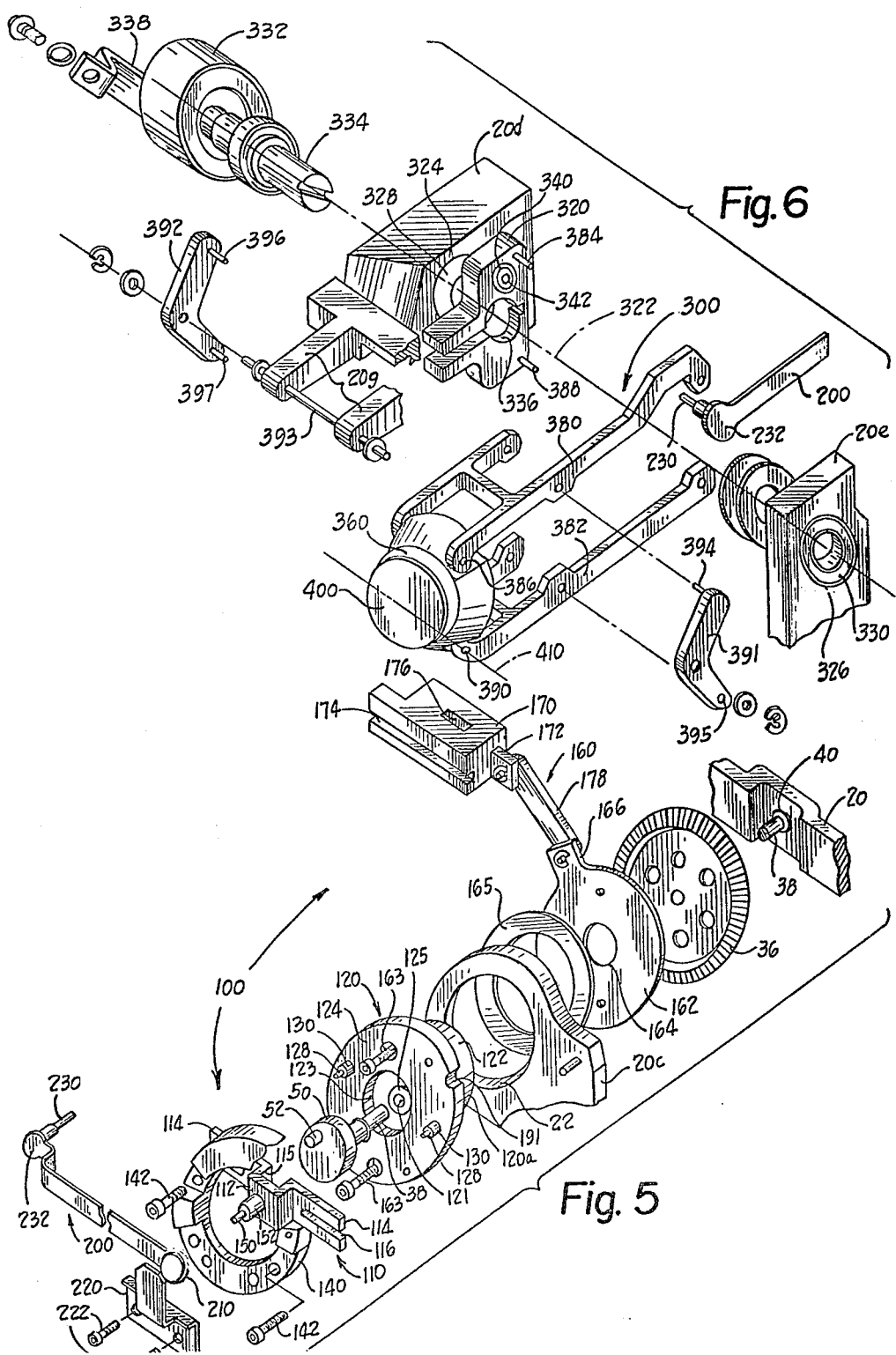

ULTRASONIC SECTOR SCANNING SEARCH UNIT

BACKGROUND OF THE INVENTION

1. Field of the Invention:

This invention relates to medical scanning apparatus and more particularly to a novel and improved ultrasonic scanning system useful for visualizing the condition of internal organs of a patient or the like.

2. Description of the Prior Art:

Ultrasonic scanning of a test object in order to examine its interior structure is known in the art. Such ultrasonic scanning relies on the use of a transducer which transmits ultrasonic energy into a subject and receives reflections of that transmitted energy. These reflections are then converted to electrical signals which typically are transmitted to a display apparatus where an image is produced on a cathode ray tube screen.

In medical diagnosis it is now routine to position a transducer in contact with a patient for conducting a study. The transducer is then rocked about an axis passing along the face of the transducer to scan a sector. The most widely used apparatus and technique used for this purpose is disclosed and claimed in U.S. Pat. No. 3,924,452 issued to Meyer and Wright on Dec. 9, 1975 and entitled "Sector Scanning Ultrasonic Inspection Apparatus".

Cardiac studies are difficult with prior apparatus such as that disclosed in the referenced patent and other devices for two major reasons. These reasons are:

1. The transducer should be pivoted quite rapidly to produce useful images. This requirement is due in large part to the rapid movement of the heart; and, 2. The transducer must be small and capable of accurate positioning at one of a few locations each between ribs of the patient.

Sector scanning devices have been proposed which are intended to be used primarily, if not exclusively, for cardiac studies. With these devices the rocking action of the transducer is achieved mechanically rather than manually as in the referenced patent. In some of these units the magnitude of sector scan is adjustable. When the sector scanning angle is relatively large a relatively broad area of the patient may be surveyed. When something of interest is noted the sector scanning angle may be reduced to focus on the region of interest. Prior units have required that the scanning operation be temporarily stopped when it was desired to adjust the magnitude of the sector being surveyed.

SUMMARY OF THE INVENTION

A scanner unit incorporating features of this invention includes a frame, a transducer, and a transducer supporting structure projecting from the frame and mounting the transducer for oscillatory movement about a virtual pivot axis. Drive means are also provided for oscillating the transducer support structure to effect the desired oscillatory movement of the transducer. Means are also employed for mechanically varying the magnitude of transducer oscillation while that oscillation is occurring.

By being able to vary the magnitude of oscillation while that oscillation is occurring the operator of the scanner unit can scan a broad sector and then narrow down his field of search without losing his place or wasting time. This offers a clear advantage over prior art mechanisms which did not allow variation of the sector scan angle during oscillation.

DESCRIPTION OF THE DRAWINGS

FIG. 1 is a plan view of a sector scanning search unit incorporating features of this invention and shown connected in an ultrasonic testing system.

FIG. 2 is a view similar to FIG. 1, with parts removed, to reveal the arrangement of components on the unit chassis;

FIG. 3 is an elevation view of the unit illustrated in FIG. 2;

FIG. 5 is an exploded view of the variable oscillation mechanism shown in FIGS. 2 and 3;

FIG. 6 is an exploded view of the transducer supporting structure shown in FIGS. 2 and 3.

DESCRIPTION OF THE PREFERRED EMBODIMENT

Figure 4:
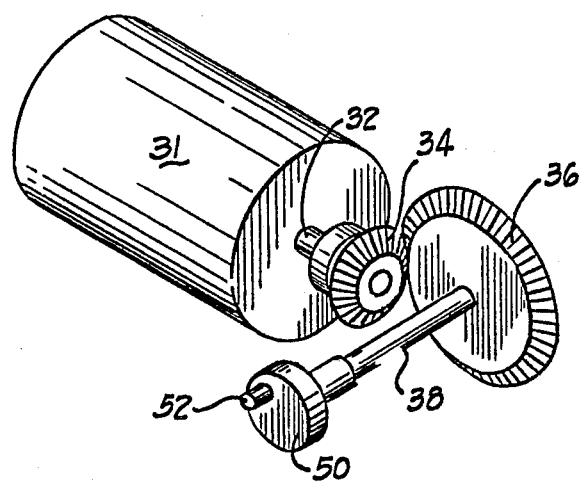
FIG. 4 is a perspective view of the power train employed in the unit of FIG. 1.

Referring to FIG. 1, a hand-held ultrasonic scanner unit 10 is illustrated which incorporates features of this invention. The unit 10 is shown connected to an ultrasonic medical diagnosis unit 12 by an electric signal/power cable 14.

The scanner unit itself includes an elongate, casing 18 which can be hand carried and manipulated. The casing 18 encases an elongate component supporting frame or chassis 20.

Referring to FIGS. 2 and 3, the unit 10 is illustrated with the casing 18 removed so that the overall arrangement of components on the chassis can be viewed. The chassis 20 supports a power train, generally indicated at 30 and shown more clearly in FIG. 4, a variable oscillation mechanism, indicated generally at 100 and shown in more detailed in FIG. 5, a driving link 200, more clearly shown in both FIGS. 5 and 6, a transducer supporting structure, indicated generally at 300 and shown more clearly in FIG. 6, and a transducer 400, also clearly shown in FIG. 6.

Power in the form of rotary motion is generated in the power train 30 and transmitted to the variable oscillation mechanism 100 which converts that rotary motion into an oscillatory motion. The driving link 200 connects the variable oscillation mechanism 100 and the transducer supporting structure 300. Any oscillating motion produced at the variable oscillation mechanism is transmitted to the driving link 200. The driving link, in turn, conveys to the support structure 300 the translational component of the oscillatory motion which is coaxial with the axis of the link 200. The translational magnitude of the component of the oscillatory motion can be varied at any time, even while oscillatory motion is being produced, merely by manually adjusting the oscillation mechanism. Translational motion of the driving link 200 is converted back to oscillatory motion by the support structure 300. The structure 300 supports the transducer 400 for oscillatory movement about a virtual pivot axis 410 extending across the face of the transducer. Consequently any translational movement of the driving line 200 is manifested as an oscillation of the transducer 400.

The power train 30 comprises a motor 31 which includes a drive shaft 32 extending axially of both the motor 31 and the chassis 20. The drive shaft 32 extends through a chassis wall portion 20a and supports a driving pinion 34 for rotation on the opposite side of the wall portion 20a from the motor 31. The driving pinion 34 is a bevel gear which meshes with and drives another bevel gear 36 supported at right angles to the driving pinion 34. The driven gear 36 is fixedly mounted to a drive shaft 38. The drive shaft 38 is rotatably supported at one end in a bearing 40 disposed in a chassis wall portion 20b. At its opposite end the drive shaft 38 supports an enlarged cylindrical head 50 which supports an offset or eccentric cam 52 (See FIG. 4).

The power train 30 produces a rotary output which must be converted into oscillatory motion to effect the desired oscillation of the transducer. The variable oscillation mechanism 100 is therefore disposed in communication with the output end of the power train 30.

Referring to FIG. 5, the output end of the power train 30, comprising the rotating eccentrically mounted cam 52, is shown in relation to the variable oscillation mechanism 100. The oscillation mechanism 100 includes separate subassemblies for converting the power train's rotary motion to oscillatory motion and for adjusting the magnitude of the oscillatory motion which is eventually transmitted to the transducer support mechanism 300.

The oscillation producing subassembly comprises a U-shaped slider member 110 which is, at the same time, confined to move linearly across a face of a hub 120 and to engage the rotating cam 52.

The hub 120 supports the output end of the power train 30 and is a guide for the slider member 110. The hub 120 is rotatably mounted to the chassis 20 coaxially of the drive shaft 38. A reduced diameter section 120a of the hub 120 is disposed within a mating circular passage 22 in a chassis wall portion 20c. A bore 121 extends axially through the hub 120 from one of its opposed faces 122 and terminates centrally of an enlarged recess 123 disposed in the hub's opposite face 124. A bearing 125, disposed within the bore 121, rotatably receives the output end of the coaxially aligned drive shaft 38. The recess 123 is dimensioned to receive the enlarged cylindrical head 50 on the output end of the drive shaft 38. The hub face 124 supports a pair of diametrically opposed pins 128 which extend axially from the face 124. The pins 128 each support a bearing 130.

The U-shaped slider member 110 is a cam follower for the cam 52. That slider member comprises a U-shaped center section 112 and a pair of oppositely entending wing portions 114. The member 110 is sidably mounted to the hub's face 124 so the recess 115, defined by the U-shaped center section, faces the recess 123 and mates with the cam 52. The wings 114 include aligned elongate slots 116 which each engage one of the bearings 130. As the cam 52 rotates within the recess 115 to slider member 110 oscillates back and forth across the hub face 124 is guided by the bearings 130 each.

A slider retainer 140 is employed to retain the slider 110 adjacent the face 124 of the hub 120 so that the slots 116 in the slider are maintained in engagement with the bearings 130 in the face of the hub. The retainer 140 is a torus shaped member which is attached to the hub face 124 with a pair of fasteners 142.

In order to transmit oscillatory motion of the slider 110 to the driving link 200, a low friction connection is provided between these components. A pin 150 is mounted to the slider center section 112 and extends outwardly through the center of the retainer 140. A bearing 152, mounted to the pin 150, mates with a loop like end portion 210 of the driving link 200. any oscillatory motion which is imparted to the slider member 110 is conveyed by this low friction connection to the driving link 200. A retainer 220 is employed to maintain the end portion 210 of the driving link in mating engagement with the bearing 152. That retainer 220 is attached to the retainer 140 by a pair of fasteners 222.

Generally speaking, oscillatory movement of the driving link 200 is produced by operating the power train 30 so that the eccentric cam 52 rotates in the recess 115 of the slider 110 which responds to such cam rotation by oscillating past the guide bearings 130 and over the recess 123. Any oscillatory movement of the slider 110 is transmitted directly to the driving link 200.

It is desirable to be able to control the amount of oscillatory motion which the driving link 200 imparts to the transducer support structure 300. The variable oscillation mechanism 100 achieves that control by means of an oscillation adjusting subassembly 160 which can control the component of oscillatory motion of the slider 110 in the direction of the longitudinal axis of the driving link 200.

The oscillation adjustment subassembly operates by selectively rotating the slider 110 with respect to the link 200. When the axis of the oscillatory motion of the slider 110 approaches or coincides with the longitudinal axis of the link 200, the component of oscillatory motion transmitted through the driving link 200 to the transducer support structure 300 will be at a maximum value. When the axis of oscillatory motion of the slider 110 is approaching a right angle with respect to the longitudinal axis of the driving link 200, the component of oscillatory motion transmitted through the link 200 to the transducer support structure 300 will be at a minimum valve.

The oscillation adjustment subassembly, indicated generally at 160 (Shown in FIG. 5), enables the hub 120 to be rotated a desired amount with respect to the chassis 20 so the slider 110, mounted to the hub, rotates with respect to the driving link 200.

The subassembly 160 comprises a plate 162 which is secured for rotation with the hub 120 by means of a pair of fasteners 163. The plate is disposed coaxially with the drive shaft 38 between the chassis wall portion 20c and the driven gear 36. An opening 164 disposed centrally in the plate, enables the drive shaft 38 to extend through the plate 162 and to rotate freely without interference. A washer 165 is interposed between the plate 162 and the chassis wall portion 20c to reduce any sliding friction which would otherwise be encountered if the plate 162 were to rub directly against the wall portion 20c. The plate 162 also includes a projection 166 which extends radially outward from the periphery of the circular plate 162.

The subassembly 160 also comprises a slider 170. The slider 170 includes an outwardly extending projection 172 and a pair of elongate guide slots 174, only one of which is shown. Referring to FIG. 2, it is seen that an elongate switch bracket 60 is attached to the chassis 20. The bracket 60 supports the slider 170 for longitudinal movement along the longitudinal axis of the chassis. The switch bracket 60 includes an elongate central recess 62 which defines a path for the slider 170. The opposed elongate side edges of the recess 62 are engaged by the slider's guide recesses 174. A slot 176 is disposed in the slider 170 so that an actuator 177 (See FIG. 1) mounted externally of the casing can mechanically engage the slider. The plate 162 and the slider 170 are interconnected by a link 178 which pivotally engages the projections 166, 172 on the plate and slider, respectively.

Operation of the oscillation adjustment subassembly to effect rotation of the hub 120 and the attached slider 110 is initiated by longitudinally moving the slider 170 in the switch bracket recess 62. The link 178 transmits this motion to the plate 162 which is then caused to rotate. Since the hub 120 and the plate 162 are directly connected to hub 120 will undergo a similar rotation, reorienting the slider 110 accordingly.

An on-off switch 180 is disposed at one end of the travel of the slider 170. The on-off switch 180 connects the power cable 14 and the motor 30. When the slider 170 is positioned at the end of its travel, as shown in FIG. 2, the switch 180 is opened and no current passes to the motor. When the slider moves from that end position, the motor 120 is activated. Defined "on" positions may be provided wherein the hub 120 and slider 110 are rotated to particular orientations and the transducer consequently oscillates over specific sector angles.

In order to locate the hub 120 in a particular orientation, a detent mechanism 190 (see FIGS. 2 and 3) is provided which is mounted to the chassis 20. A plurality of notches, only one of which is shown at 191, are provided at particular points along the periphery. Each notch is related to a particular magnitude of sector scan for the transducer. For example, notches may be provided to produce transducer sector scans of 20°, 30°, 45°, and 60° respectively. Indicia may be put on the casing (See FIG. 1) to indicate these positions. Interengagement of the detent mechanism 190 with one of the notches 191 locates the hub 120 and slider 110 in a particular orientation.

The detent mechanism 190 is shown in detail in FIGS. 2 and 3. A detent arm 192 is provided which is pivotally mounted at one end of the chassis 20 and positioned so that it is located adjacent the periphery of the hub 120. The detent arm 192 carries a bearing 194 which is adapted to engage a selected one of the notches in the hub periphery in order to locate the hub. A spring 196 interconnects the opposed end of the detent arm 192 to the switch bracket 60. The spring 196 resiliently biases the detent arm 192 toward the hub 120 so the bearing 194 is urged into running engagement with the periphery of the hub 120. Consequently, the bearing 194 will be resiliently urged into whichever hub periphery notch passes under the bearing as the hub 120 is rotated by manipulation of the actuator 177. Advantageously, while the motor is on and oscillatory motion is being generated and transmitted to the transducer support structure 300, the subassembly 160 enables the hub to be simultaneously rotated so the magnitude of the oscillatory motion being so transmitted can be varied.

The transducer structure 300, the which oscillatory motion is transmitted by the driving link 200 comprises a pantographic frame structure which is supported in centilevered fashion from one end of the chassis 20. That transducer supporting structure supports the transducer 400 for oscillatory movement about a virtual pivot axis 410 which extends medically across the transducer face. Basically, the pantographic frame comprises six pivotally interconnected links 320, 360, 380, 382, 391, 392 arranged in parallelogram fashion for movement with respect to each other when motion is applied to one of the links. the pantographic frame linkage is shown in detail in FIG. 6 and schematically in FIG. 7.

A first link 320 comprises a split hub bell crank which is intended to be mounted to a potentiometer 332. Portions 20d and 20e of the chassis 20 include apertures 324, 326 which are coaxially aligned with an axis 322. The apertures 324, 326 each receive similar coaxially aligned bearings 328, 330. The potentiometer 332, clamped to the chassis by a bracket 338, has a shaft 334 which is disposed coaxially with the axis 322 and supported in the bearings 328 and 330. The split hub bell crank is disposed between the chassis portions 20d and 20e. An aperture 336 in the bell crank 320 is positioned coaxially with the axis 322 and the bell crank 322 is clamped to the potentiometer shaft 334 by a clamping screw 335 (See FIG. 2). The first link 320 also includes an aperture 340 offset from the aperture 336. The aperture 340 supports a bearing 342 which receives a pin 230 extending from one end 232 of the driving link 200.

A second link 360 comprises a transducer supporting link for receiving and removably supporting the transducer 400. The second link lies in opposed relation to and parallel with the first link 320.

An intermediate pair of links 380, 382 interconnect the first and second links 320, 360, to close the parallelogram. The link 380 is connected to the first link 320 at pin 384. The link 380 is connected to the second link at pin 386. The link 382 is connected to the first link 320 at the pin 388. The link 382 is connected to the second link 360 at pin 390. Note that the intermediate links 380, 382 are each chosen to have a distored H-shape for increased rigidity of the pantographic linkage. Such an H-shaped structure permits the second link 360 to be pinned a four points. It also facilitates the use of two intermediates cranks, discussed hereinafter.

An intermediate crank structure comprises a pair of cranks 391, 392 which are mounted intermediate their ends to a shaft 393 supported by a chassis portion 20g. The intermediate crank members 391, 392 include pins 394, 395 and 396, 397, respectively, at their opposed ends, which pins engage the respective intermediate links 380, 382 at points between the ends of those intermediate links.

The relative orientation of the pivot points in the transducer supporting structure 300 facilitates oscillation of the transducer 400 about the virtual pivot axis 410 which extends across the face of the transducer 400 medially of the extremities of the transducer face. When that transducer face is circular, the virtual pivot axis 410 coincides with a line running diametrically through the center of the face.

Figure 7:
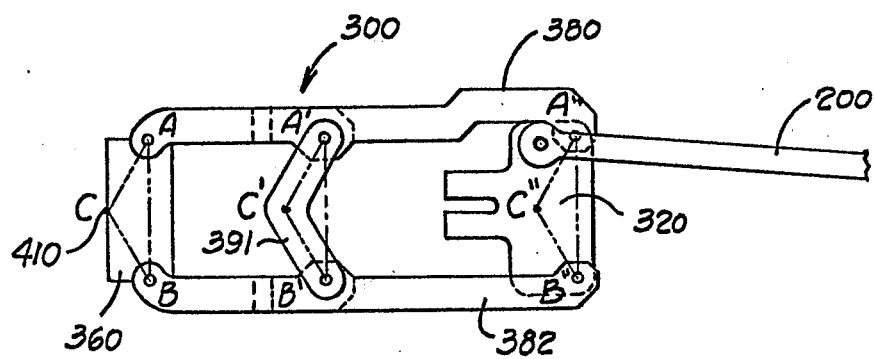
FIG. 7 is a simplified elevation view of the transducer supporting structure illustrating the relative orientations of the pivot axes of the linkage comprising the structure.

Referring to the schematic illustration of the structure 300 in FIG. 7, it is noted that points on the pivot axes of the transducer supporting link 360 form the vertices of a triangle ABC. Note that the point C indicates the virtual pivot axis 410 extending across the face of the transducer. Similarly, points on the pivot axes of the intermediate links 391, 392 form the vertices of a triangle A' B' C'. Finally, it is noted that the points on the pivot axes of the bell crank 320 form the vertices of a triangle A" B" C". Note that both point C' and C" indicate fixed pivot axes through shafts about which the intermediate cranks 391, 392 and the bellcrank 320, respectively rotate. All three of these triangles are congruent and remain congruent, irrespective of the orientation of the respective links of the support structure 300.

Other geometric relationships of the pivot axes of the transducer support structure 300 are also worthy of note. The pivot axes through the points, C, C', and C" always lie parallel to each other and in a common plane. Also, the pivot axes through the points A, A', and A" are always parallel and coplanar. The same holds true for the pivot axes through the points, B, B', and B". Finally, a plane through the pivot axes containing the points A, A' and A" is parallel to a plane through the pivot axes containing the points B, B', and B".

When a transducer supporting structure 300 incorporates these geometric relationships and when such a structure is pinned to a chassis at C", C', the result is that any oscillation imparted to the first link 320 will be transmitted without distortion to the second link 360. Though the link 360 is not pinned at its pivot point C, that pivot point bears the same relation to the pivot points A, B as the pivot point C" bears to the pivot points A", B". In other words, though on physical structure coincides with the axis 410, that axis is fixed. The link 360 can be structured to support the transducer 400 so that the transducer face lies on this fixed virtual pivot axis 410 through point C and so that axis 410 passes medially of the extreme ends of the surface 410. Given a conventional circular transducer surface, the surface can be oriented so half of that surface will lie above the axis 410 and half of that surface will lie below the axis 410. When any oscillatory motion is imparted to the link 360 supporting such a transducer, there will be a minimum amount of transducer wiping movement about the transducer's pivot axes. Consequently, there will be a minimum amount of irritation on the skin of the patient being examined.

In the operation of this unit, movement of the actuator 177 from the "off" position to one of the "on" positions (e.g., 20°, 30°, 45°, or 60°) permits the switch 180 to close, thus conducting electric power from the cable 14 to the power train 30 at the motor 31. When the motor 31 starts operating, the gear 34 rotates and effects rotation of the mating gear 36 and the drive shaft 38 mounting gear 36. The eccentrically mounted cam 52 rotates with the drive shaft 38 and effects translational oscillation of the slider member 110. That oscillatory motion is transferred to the driving link 200 connected the slider member 110.

The actuator 177 is connected to the slider member 110 by the oscillation adjustment subassembly 160. Movement of the actuator 177 effects rotation of the slider into any one of a number of distinct positions in which the orientation of the slider member 110 is varied with respect to the driving link 200 so that the component of oscillatory motion which extends along the axis of the link 200 is varied.

The link 200 is connected to the first link or bell crank 320. Oscillatory motion transmitted to the link 320 by the link 200 is transmitted to the second or transducer supporting link 360. The orientation of the elements and pivot axes of the supporting structure 300 is such that rotation of the first link 320 about the axis of the potentiometer shaft 334 produces corresponding rotation of the transducer support link 360 and its transducer 400 about the fixed virtual pivot axis 410. With this arrangement there is no physical structure located in close proximity to the transducer surface which may interfere with positioning of the transducer against the patients body. Yet, the axis 410 is located on and centrally of the transducer face so that the transducer is enabled to oscillate about that fixed axis and minimize wiping action against the body of the patient.

The adjustable oscillation subassembly 160 enables the magnitude of transducer oscillations to be varied even while the search unit is scanning so the operator can easily move from a broad sector scan to a narrower one without losing his location or wasting time.

Another advantage of this structure is that it is easily manipulable to examine a patient. Its elongate chassis facilitates manipulation. The oscillating transducer being supported axially outward and endwise of the chassis and the transducer face oriented transverse to the longitudinal axis of the chassis means that the chassis itself will not interfere with the body of a patient being examined. Consequently, most any area of the body can be subjected to examination by the oscillating transducer of this apparatus.

Although the invention has been described with a certain degree of particularity, it is understood that the present disclosure of the preferred embodiment has been made only by way of example and that numerous changes in the details of construction and the combination and arrangement of parts may be resorted to without departing from the spirit and the scope of the invention as hereinafter claimed.

What is claimed is:

1. An ultrasonic scanner unit, comprising:
   (a) a frame;
   (b) a transducer;
   (c) transducer support structure projecting from said frame and mounting said transducer for oscillatory movement about an axis;
   (d) drive means for driving said transducer support structure to effect oscillatory movement of said transducer about said axis; and
   (e) oscillation varying means operatively interposed between said transducer support structure and said drive means for mechanically varying the magnitude of transducer oscillation while said drive means is driving said transducer support structure.

2. The ultrasonic scanning unit of claim 1 where the oscillation varying means comprises an adjustable control element which controls the extent of oscillation of said transducer, said element movable to a position for fixing the transducer relative to the frame.

3. An ultrasonic scanner unit, comprising:
   (a) a frame;
   (b) a transducer;
   (c) a transducer support structure projecting from said frame and mounting said transducer for oscillatory movement about a virtual pivot axis;
   (d) drive means for oscillating said transducer support structure to effect oscillatory movement of said transducer about said virtual pivot axis;
   (e) said drive means comprising:
      (i) a source of power mounted to said frame; and
      (ii) an oscillatory driving link connected to said transducer support structure; and,
   (f) means for mechanically varying the magnitude of oscillation while the oscillation is occurring, said oscillation varying means interconnecting said source of power and said oscillatory driving link for variably controlling the amount of oscillation imparted to said driving link.

4. The ultrasonic scanning unit of claim 3 where the means for mechanically varying the magnitude of oscillation comprises an adjustable control element for varying the extent of oscillation of said transducer, said element movable to a position for fixing the transducer relative to the frame.

5. The scanner unit of claim 4 wherein said source of power terminates in a rotatable, shaft mounted eccentric and wherein further said oscillation varying means includes a connecting member which coacts with both said eccentric and said driving link, said connecting member oscillating over a fixed distance in response to rotation of said eccentric, the orientation of said connecting member with respect to said driving link being variable to vary the component of oscillatory movement of said connecting member which is transmitted to said driving link.

6. The scanner unit of claim 5 wherein said connecting member comprises a slider which is assembled to one face of a rotatable hub, said hub face including a recess for receiving said rotatable eccentric, said slider including a slot communicating with said recess, said eccentric mating with said slot for imparting translational sliding motion to said slider across said hub face, said hub slider assembly being rotatable through a range of positions to variously orient the axis of translational movement of said slider with respect to the axis of oscillatory movement of said driving link.

* * * * *